United States Patent [19]

Lindgren et al.

[11] 4,402,324

[45] Sep. 6, 1983

[54] BIOPSY NEEDLE GUIDE FOR SECTOR SCANNER

[75] Inventors: Gunnar Lindgren, Upsala, Sweden; Richard E. Molesworth, Englewood; Jack R. Sorwick, Parker, both of Colo.

[73] Assignee: Technicare Corporation, Solon, Ohio

[21] Appl. No.: 278,514

[22] Filed: Jun. 29, 1981

[51] Int. Cl.³ .............................................. A61B 10/00
[52] U.S. Cl. .................................. 128/660; 128/653; 73/620; 367/103
[58] Field of Search ........................ 128/749, 751–755, 128/660, 661, 329 R, 24 A, 763, 662–663, 653, 657; 73/620, 622, 627, 629; 367/103–104, 151, 910

[56] References Cited

U.S. PATENT DOCUMENTS

| 3,556,079 | 1/1971 | Omizo | 128/24 A X |
| 3,721,227 | 3/1973 | Larson et al. | |
| 4,029,084 | 6/1977 | Soldner | 128/760 X |
| 4,058,114 | 11/1977 | Soldner | 128/754 X |
| 4,108,165 | 8/1978 | Kopp et al. | 128/24 A X |
| 4,245,511 | 1/1981 | Soldner | 128/660 X |
| 4,249,539 | 2/1981 | Vilkomerson et al. | 128/754 X |
| 4,269,176 | 5/1981 | Beyer et al. | 128/24 A |
| 4,330,874 | 5/1982 | Sorwick | 128/660 X |

OTHER PUBLICATIONS

Lindgren; "Ultrasonically Guided Punctures"; *Radiology*; vol. 137, No. 1, pp. 235–237; Oct. 1980.

Primary Examiner—Lee S. Cohen
Assistant Examiner—Angela D. Sykes
Attorney, Agent, or Firm—W. Brinton Yorks, Jr.

[57] ABSTRACT

An ultrasound sector scan imaging system employing a hand held scan unit is provided with an adapter mounting which is affixed over the scan section, and a sterile glove or boot which encloses the scanner and the mount. A disposable needle guide mechanism is fitted, saddle style, to the mounting over the boot. The disposable guide has a channel for locating the biopsy needle in the sector scan plane, and a depression therein for hand-maintenance of the needle in the guide, during the needle location process, and for free removal of the scanner once the desired position is achieved.

7 Claims, 5 Drawing Figures

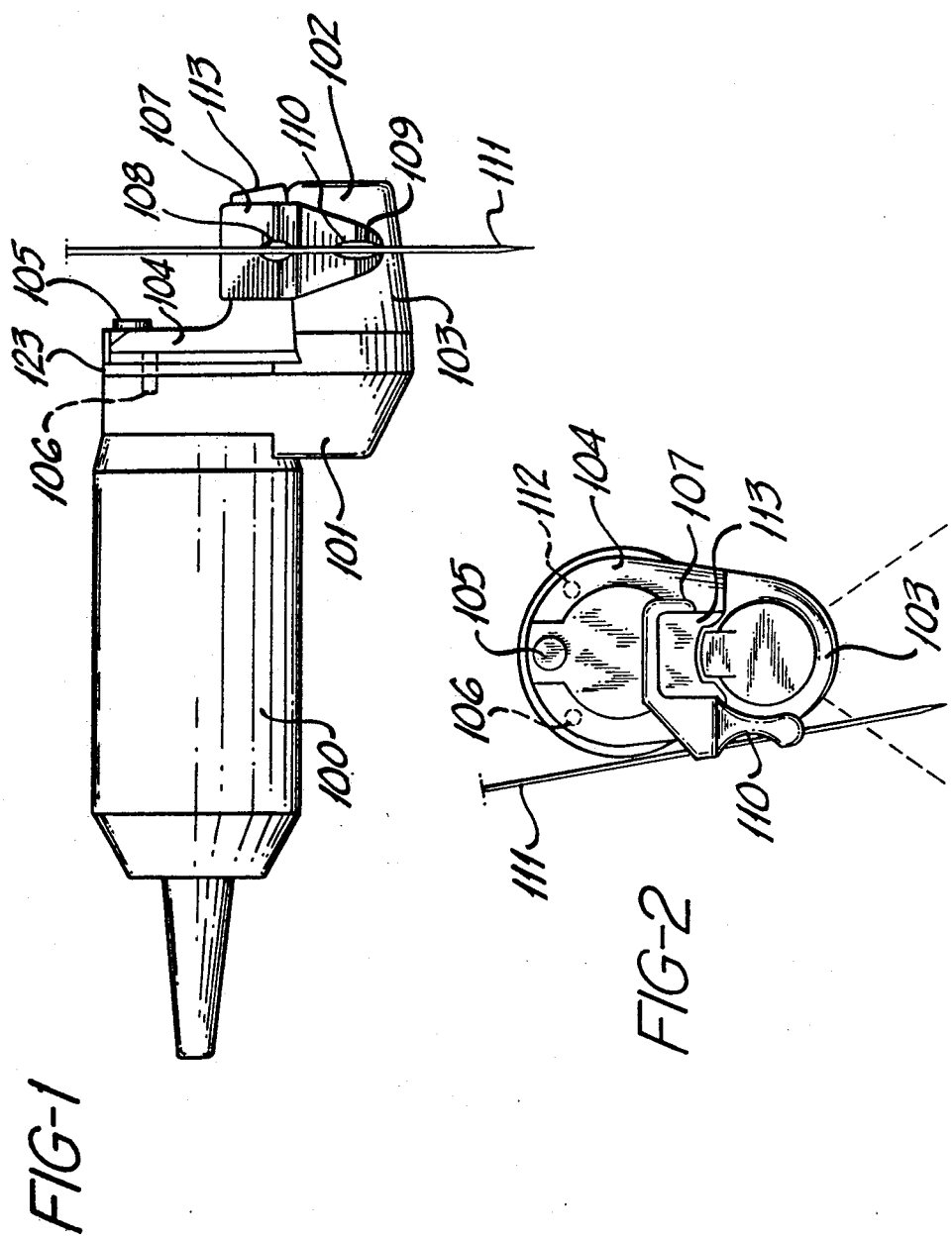

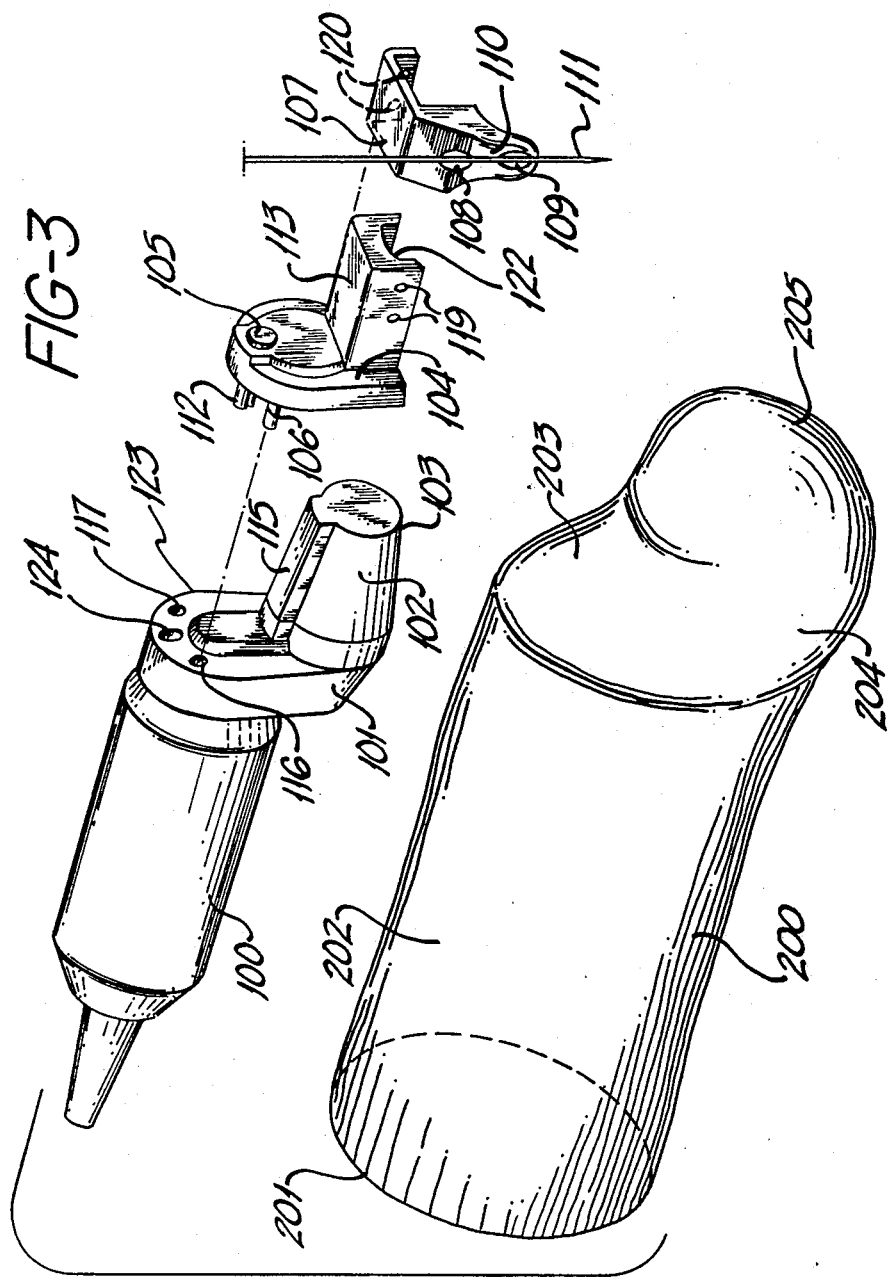

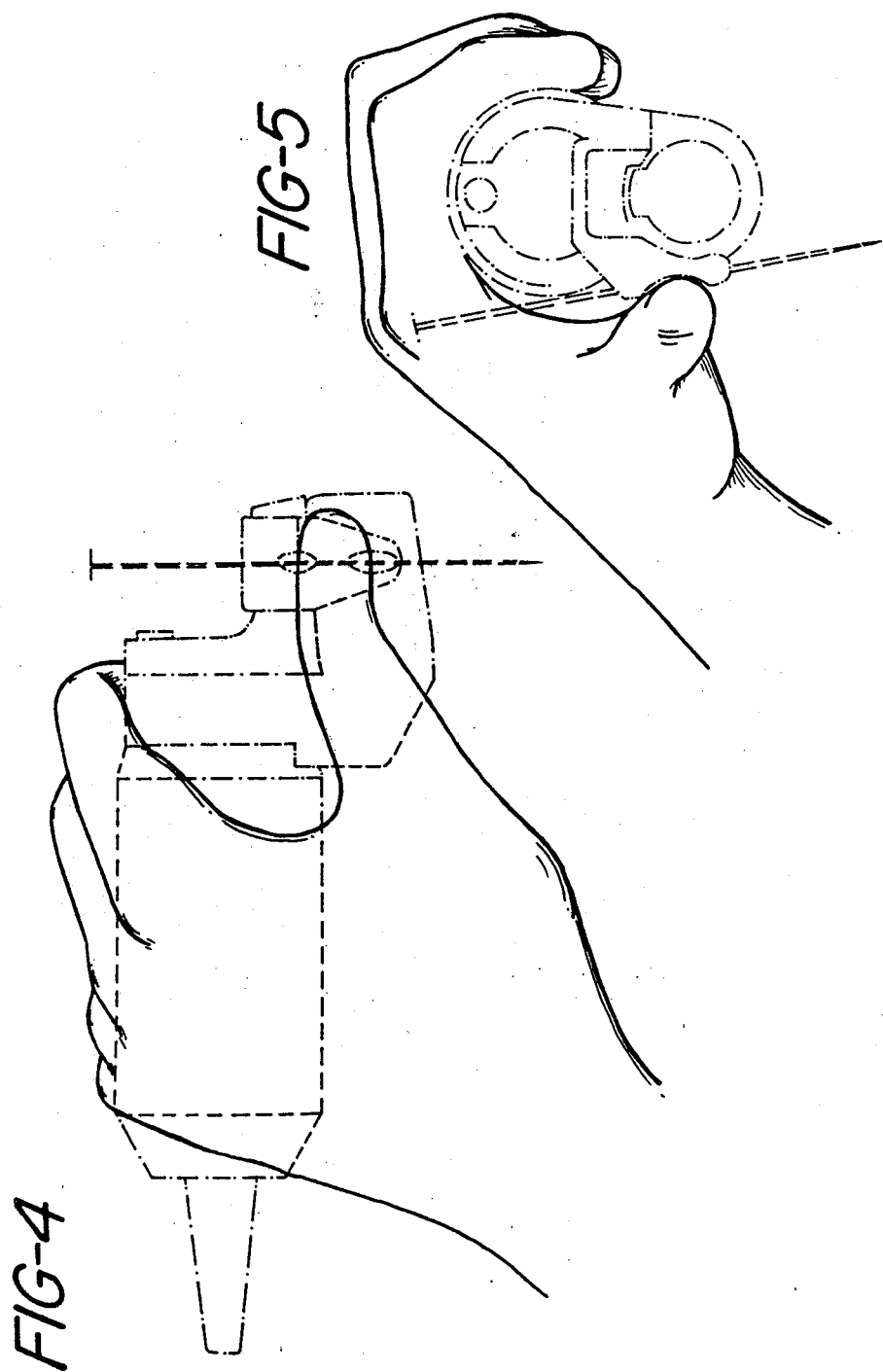

BIOPSY NEEDLE GUIDE FOR SECTOR SCANNER

BACKGROUND OF THE INVENTION AND THE PRIOR ART

A conventional technique for obtaining tissue samples from within the body is aspiration biopsy. This technique is safe and minimally traumatic, utilizing a small, hollow needle which is inserted directly into the body to a desired point, whereupon a tissue sample is withdrawn, such as by vacuum aspiration. The needle is then withdrawn, but because of its relatively insignificant diameter, wound closure occurs substantially normally by muscular and tissue tension, generally without the need for sutures, cauterization, or the like.

For optimal effectiveness, of course, this technique requires that the tip of the needle be precisely accurately placed at the location of the tissues to be sampled, and it is a primary object of the principles of the present invention to provide means and methods for facilitating such placement.

Because of their superior imaging capability with minimal hazard or risk to the patient, ultrasound imaging techniques have achieved prominent use for the location of the needle during biopsy techniques. In one class of prior art system, exemplified by U.S. Pat. Nos. 3,721,227 to Larson et al., 4,108,165 to Kopp et al., 4,029,084 to Soldner, and German Pat. No. 24 55 401 to Videnskaber, a biopsy needle is inserted in the center of an ultrasound transducer or transducer array, parallel to the direction of propogation of the ultrasound energy, so that the biopsy needle shows on the ultrasound image only if it diverts from such parallel orientation.

In another class of prior art system, exemplified by U.S. Pat. No. 4,058,114 to Soldner, the biopsy needle is carried by angular aiming apparatus which in turn is mechanically coupled to a pointer overlying the ultrasound image field. As the needle angle is established, the pointer overlays the image and follows the progress of the needle.

In yet another class of prior art system, exemplified by U.S. Pat. Nos. 3,556,079 to Omizo and 4,249,539 to Vilkomerson et al., a transducer element at the skin and another one within or at the tip of the needle correspond with one another precisely to locate the needle in the image field.

These prior art systems have varying degrees of propriety and efficiency, depending upon the ultrasound system being utilized and the needs or requirements of the operating surgeon. Perhaps the least efficient are those which require parallel orientation of the propogating ultrasound energy and the needle, because of their failure to yield either clear composite images or accurate needle depth representation. Probably the most effective prior art systems are those exemplified by the Vilkomerson et al. patent, but they require special electronics and compact and expensive transducer elements mountable at the needle tip and removable through the biopsy needle.

It is an object of the present invention to provide ultrasonically guided biopsy needle systems and techniques which yield highly visible and well calibrated images including the needle during insertion, but which do not require separate active transducer elements associated with the needle.

Recently, a class of real time ultrasound imaging systems have become popular based on the sector scan rationale. For example, one such system is commercially available from Technicare Corporation under the tradename "AUTOSECTOR", and is exemplified in U.S. application Ser. No. 178,488 of Sorwick filed Aug. 15, 1980 now U.S. Pat. No. 4,330,874. Generally, sector scan systems employ rotating or oscillating transceiver mechanisms for sonic illumination of, and hence imaging of a sector of tissue which broadens with increasing distance from the transceiver. In the Sorwick style system, a stationary transducer and an oppositely facing, rotating inclined sonic mirror are located in a first, outboard portion of a scanner, the motor drive and control systems are located in a second, inboard portion of the scanner, and the outboard and inboard scanner are coupled in offset relationship by an intermediate section which transfers oscillatory motive force from the motor to the mirror/transducer section. The whole unit is conveniently hand held, but only the smaller, spatially offset outboard portion makes contact with the patient.

It is an object of the present invention to provide biopsy needle guide apparatus and techniques adapted for use in conjunction with sector scan systems, and more particularly those of the sort exemplified by the captioned Sorwick application.

Associated, but by no means less significant objects of the present invention, include provision of a design which avoids the need to sterilize the ultrasound scanner to be used in biopsy procedures, provision of guide systems which are not only precise, but are sufficiently inexpensive to permit disposability, and provision of guide mechanisms which protect valuable transducer head mechanisms, and avoid damage or misalignment due to forces to which the scan head is subjected during the biopsy procedure.

SUMMARY OF THE INVENTION

In accordance with the principles of the present invention, a sector scan head such as the type described and claimed in U.S. application Ser. No. 178,488 of Sorwick is provided with an adapter mount which nestles over the transceiver-scan portion of the scan head, but which is affixed to the more rugged motor drive and intermediate transfer sections of the scan head. A disposable, sterile boot or glove is fitted over this portion of the assembly. A disposable biopsy needle guide snaps over the boot and onto the adapter/mount in saddle fashion, with at least one portion extending along the side of the transceiver and forming a guide channel or groove in the plane of the sector image. A depression in the needle guide allows the surgeon to hold the needle in the guide channel or groove with the same hand which holds the scan head, depressing it into the body of the subject during the imaging process. Once the needle is in place, the entire scan head may be readily removed, the needle guide portion and the boot discarded, biopsy procedure completed, and the sector scan head be maintained for subsequent use.

In operation, a composite tissue-needle image occurs because the inwardly penetrating needle is located in the sector plane, but is inclined with respect to the outwardly directed, radial scan lines of the sector. Thus, the progressing discontinuity between the needle point and the tissue provides a point of sonic reflection, and hence appears on the composite image as a bright spot. In this fashion, the procedure is conducted with a high degree of reliability and certainty of location.

DESCRIPTION OF THE DRAWINGS

FIGS. 1 and 2 show respective side and end views of a preferred embodiment of the principles of the present invention, omitting for clarity a sterile botto enclosure of portions of the apparatus.

FIG. 3 shows an exploded perspective view of a preferred embodiment of the principles of the present invention, further including the disposable protective boot.

FIGS. 4 and 5 show respective side and end views of the embodiment of FIGS. 1 through 3, absent the protective boot, illustrating a mode of use.

BEST MODE FOR CARRYING OUT THE INVENTION

Referring to the drawings in the aggregate, there will be seen a preferred embodiment of the principles of the present invention, designed to operate in conjunction with a sector scanner of the type described and claimed in the previously referenced U.S. application of Sorwick. As noted, such a sector scan head includes a first, inboard portion 100, which encloses motor drive and control mechanisms for the scanner. An outboard portion 102, which is offset from inboard portion 100, attached in axially offset fashion to the inboard portion 100 by means of an intermediate portion 101, contains the transducer-mirror apparatus whereby sector scanning may be achieved. The scan window 103, which contacts the patient, is situated at the lowermost portion of the outboard portion 102. As described in the Sorwick application, the intermediate section 101 contains belts or the like drive mechanisms whereby motive power is transferred from the motor in the inboard section 100 to an oscillating sonic reflector in the outboard section 102. Over the intermediate portion 101 is a cover 123 enclosing said drive mechanism. To the extent required to complete the disclosure hereof, the disclosure materials of the Sorwick application (which is also assigned to the assignee) are expressly incorporated by reference herein.

In commercial embodiments of the sector scan apparatus as described in the Sorwick application, the outboard portion 102 includes a raised land 115 and the intermediate portion 101 includes a pair of holes 116 and 117, generally for attachment of the scan head to B-scan arms or the like. Such attachment forms the basis of yet another copending application assigned to the assignee hereof, U.S. application Ser. No. 178,487.

In accordance with the principles of the present invention, a reusable mounting adapter 104 (e.g., of machined metal) is provided for precision fit against portions 101, 102, 123 of the scan head. In particular, the adapter 104 has a lowermost channel 122 which clears the raised land 115 of section 102 of the scan head, and a pair of bayonet pins 106 and 112 which fit into the openings 116 and 117 of the scan head. A release wheel 105 in the adapter mount 104 operates in a rotating fashion to cause the member 112 to move axially to provide a clamping action against the inside surface of cover 123 through an opening 124 in cover 123 to hold the pins 106 and 112 within the openings 116 and 117. Hence, the adapter mount may be quickly, accurately, and rigidly affixed to the scan head as is most clearly evident from FIG. 1. It will be noted that, in such an arrangement, the chief mechanical connection, by way of the pins 106 and 112, is directly to the relatively less fragile portions 101, 123 and 100 (i.e., in the aggregate, a "first portion") of the scan head.

The biopsy sampling technique is of course a sterile procedure, and it is therefore necessary either to provide sterile conditions either by sterilization of the scan head itself, or, more desirably, by providing a sterile barrier between the scan head and the patient. In accordance with preferred embodiments of the principles of the present invention, a sterile, disposable boot or glove 200 (see FIG. 3) is provided for enclosure of the scan mechanism and the adapter mount 104 thereon. As noted in FIG. 3, the glove or boot includes an opening 201 through which the scan head and adapter 104 are placed, and a configuration 202, 203, and 204 generally conforming to the shape of the scan head mechanism. The boot or glove is closed at an end 205 opposite the opening 201. In preferred embodiments, the boot or glove 200 is composed of a sonically transparent material, such as silicone rubber or the like, and is sonically coupled to the sector scan window 103 of the scanner in conventional fashion, by provision of a coupling gel, oil, or the like between the window 103 and the interior of the boot or glove 200. Likewise, it is anticipated that coupling gel or oil will be utilized, in conventional fashion, on the outer surface of the boot or glove 200 to facilitate sonic continuity between the window 103 and the body of the patient.

For clarity of explanation, the boot or glove 200 is not included in the illustrations of FIGS. 1, 2, 4, and 5, but it is understood that in preferred operation, the boot or glove 200 will be employed.

With further reference to the drawings, a preferred embodiment of the principles of the present invention includes a disposable needle guide 107 (e.g., if disposable plastic), which snaps in saddle fashion over the portion 113 of the adapter 104 (and over the flexible boot or glove 200). In preferred form, the adapter mount 104 defines depressions 119, for snap locking with raised lands 120 on the needle guide 107. Hence, as will be most readily appreciated from FIG. 2, the needle guide is sterile and is mounted "in saddle fashion" over the adapter mount 104 (and also over the sterile boot or glove), and is there held in precisely aligned disposition.

The needle guide defines, in a downwardly extending protuberance on one side thereof, a "V" groove or channel 108 and 109 which is adapted to receive a biopsy needle 111, and is shown in the drawings. Between the portions 108 and 109 of the needle guide or channel is a transverse depression 110, whereby the thumb or the like of the surgeon will maintain the needle 111 in position in the guide channel 108 or 109 by simple, direct pressure. By grasping the top of the needle 111 with the other hand, the surgeon can depress the needle 111 into the body of the patient.

As will be noted from the phantom lines which define the image sector in FIG. 2, the needle 111 penetrates the sector, and hence the body of the patient at the segment being imaged. Referring to the side view of FIG. 1, the scan plane is defined in parallel by the line of the needle 111.

Finally, it will be appreciated that a screen transparency overlay may be provided for the ultrasound system, which includes color enhanced or the like areas defining the possible area of travel of the needle. The surgeon's work will thereby be simplified, in that he needs only to view the portion of the image display through which needle passage may occur.

The foregoing has set forth preferred and illustrative embodiments of the principles of the present invention but it is to be understood that numerous alternative embodiments will occur to those skilled in the art without departure from the spirit or scope of the present invention.

We claim:

1. For use in an ultrasound sector scan imaging system employing a scan head having at least a first portion for providing motive power, and a second portion, connected to and axially offset generally downwardly from said first portion, carrying a transceiver for imaging a sector area in a plane normal to and below a common axis of said first and second portions, apparatus for utilizing said scan head and imaging system in a biopsy procedure comprising:

adapter means, fixedly, removably mountable to said first portion and including an integral segment extending along and generally above said second portion; and guide means, detachably fixedly mountable to said integral segment, said guide means including a downwardly extending protuberance intersecting the plane of said sector area alongside said second portion, said protuberance defining a groove, adapted to receive a biopsy needle, said groove lying in said plane, said protuberance further defining a depression, transversely intersecting said groove, and facing outwardly from alongside said second portion, for pressured maintenance of a needle in said groove;

whereby a needle, when maintained in said groove, and guided downwardly into the sector area, proceeds through said sector plane obliquely to scan lines from said scan head.

2. Apparatus as described in claim 1 and further comprising barrier means for enclosing said scan head and said adapter means, said guide means being mountable to said adapter means over said barrier means.

3. Apparatus as described in claim 2 wherein said barrier means and said guide means are sterile and said scan head and adapter means are non-sterile.

4. For use in an ultrasound sector scan imaging system employing a scan head having at least a first portion for providing motive power, and a second portion; connected to and axially offset generally downwardly from said first portion, carrying a transceiver for imaging a sector area in a plane normal to and below a common axis of said first and second portions, a kit for utilizing said system for biopsy procedures comprising:

adapter means, fixedly, removably mountable to said first portion and including an integral segment extending along and generally above said second portion;

guide means, detachably fixedly mountable to said integral segment, said guide means including a downwardly extending protuberance intersecting the plane of said sector area alongside said second portion, said protuberance defining a groove, adapted to receive a biopsy needle, said groove lying in said plane, said protuberance further defining a depression, transversely intersecting said groove, for pressured maintenance of a needle in said groove; and barrier means for enclosing said scan head and said adapter means, said guide means being mountable to said adapter means over said barrier means.

5. A kit as described in claim 4 wherein said barrier means and said guide means are sterile, and said scan head and adapter means are non-sterile.

6. For use in an ultrasound sector scan imaging system employing a scan head having at least a first portion for providing motive power, and a second portion, connected to and axially offset generally downwardly from said first portion, carrying a transceiver for imaging a sector area in a plane normal to and below a common axis of said first and second portions, and adapter means, fixedly, removably mountable to said first portion and including an integral segment extending along and generally above said second portion, a kit for utilizing said system for biopsy procedures comprising;

guide means, detachably fixedly mountable to said integral segment, said guide means including a downwardly extending protuberance intersecting the plane of said sector area alongside said second portion, said protuberance defining a groove, adapted to receive a biopsy needle, said groove lying in said plane, said protuberance further defining a depression, transversely intersecting said groove, for pressured maintenance of a needle in said groove; and barrier means for enclosing said scan head and said adapter means, said guide means being mountable to said adapter means over said barrier means.

7. For use in an ultrasound sector scan imaging system employing a hand held scan head having at least a first portion for providing motive power, and a second portion connected to and axially offset generally downwardly from an end of said first portion, and having left and right sides and an end remote from said connection to said first portion, and carrying a transceiver for imaging a sector area in a plane normal to and below axes of said first and second portions which share a common plane, apparatus comprising:

an adapter means fixedly removably mountable to said first portion and including an integral segment extending along and generally above said second portion; and a disposable needle guide means, detachably fixedly snap-mountable on said integral segment, said guide means including a protuberance extending downwardly along one side of said second portion when mounted, said protuberance including a needle groove located in a plane which includes said plane of said sector area, and a depression facing outwardly from said one side of said second portion which transversely intersects said groove for pressured maintenance of a needle in said groove, whereby a needle, when maintained in said groove and guided downwardly into the sector area, proceeds through said sector plane obliquely to scan lines from said scan head.

* * * * *